(12) United States Patent
Laban et al.

(10) Patent No.: US 7,208,609 B2
(45) Date of Patent: Apr. 24, 2007

(54) METHOD FOR PRODUCING THIOCTIC ACID

(75) Inventors: Gunter Laban, Dresden-Langebrück (DE); Peter Meisel, Dresden (DE); Gilbert Müller, Offenbach (DE)

(73) Assignee: MEDA Pharma GmbH & Co. KG, Bad Homburg (DE)

( * ) Notice: Subject to any disclaimer, the term of this patent is extended or adjusted under 35 U.S.C. 154(b) by 260 days.

(21) Appl. No.: 10/501,729

(22) PCT Filed: Jan. 7, 2003

(86) PCT No.: PCT/EP03/00064

§ 371 (c)(1),
(2), (4) Date: Dec. 7, 2004

(87) PCT Pub. No.: WO03/059902

PCT Pub. Date: Jul. 24, 2003

(65) Prior Publication Data

US 2005/0107620 A1    May 19, 2005

(30) Foreign Application Priority Data

Jan. 16, 2002    (DE) ................................ 102 01 464

(51) Int. Cl.
C07D 339/02    (2006.01)
(52) U.S. Cl. ......................................................... 549/39
(58) Field of Classification Search ................... 549/39
See application file for complete search history.

(56) References Cited

U.S. PATENT DOCUMENTS

| 4,797,298 A | 1/1989 | Brennan et al. |
| 6,013,833 A | 1/2000 | Gewald et al. |
| 6,229,042 B1 | 5/2001 | Gewald et al. |
| 6,288,106 B1 * | 9/2001 | Pearson et al. ............. 514/440 |
| 6,313,164 B1 * | 11/2001 | Fujita et al. ................ 514/440 |
| 6,441,024 B1 * | 8/2002 | Klatt et al. ................. 514/440 |
| 6,462,202 B1 * | 10/2002 | Schuhbauer et al. .......... 549/39 |
| 6,844,449 B2 * | 1/2005 | Laban et al. .................. 549/39 |
| 6,844,450 B2 * | 1/2005 | Salvi et al. ................... 549/39 |
| 6,864,374 B2 * | 3/2005 | Villani et al. ................. 549/39 |
| 7,030,251 B2 * | 4/2006 | Laban et al. .................. 549/39 |
| 7,109,362 B2 * | 9/2006 | Klatt et al. ................... 554/87 |

FOREIGN PATENT DOCUMENTS

| DE | 195 33 881 A | 3/1997 |
| DE | 196 01 787 C | 7/1997 |
| DE | 197 09 069 C2 | 9/1998 |

OTHER PUBLICATIONS

Bulman Page PC:, "An enatioselective synthesis of R-(+)-alpha lipoic acid", Journal of Chemical Society Perkin Transactions I 1999, XP009010605 USA, pp. 1615-1618.
Gopalan AS et al., "Baker's yeast reduction of alkyl 6-chloro-3-oxohexanoates: synthesis of (R)-(+)-alpha lipoic acid", Journal of Chemical Society Perkin Transactions I 1990, XP009010601 USA, pp. 1897-1900.
Brookes MH et al., "Synthesis of alpha-(R)-and alpha-(S)-lipoic acid from (S)-malic acid", Journal of Chemical Society Perkin Transactions I 1988, XP009010600 USA, pp. 11.
Dhar P et al., "Piperidinium tetrathiothungstate as sulfur transfer reagent: synthesis of cyclic disulfides", Journal of Organic Chemistry, 57, 1992, XP002241606 USA, pp. 1699-1702.
Crump DR, "Synthesis of (2S)-2-propylthietan", Australian Journal of Chemistry, vol. 35, 1982,, pp. 1945-1948, XP002241607 Australia.

* cited by examiner

*Primary Examiner*—Deborah C. Lambkin
(74) *Attorney, Agent, or Firm*—Ann S. Hobbs; Venable LLP

(57) ABSTRACT

The invention relates to a method for producing pure racemic, R- or S-thioctic acid or mixtures thereof by reacting 6,8-disubstituted octanoic acid or their salts or esters with sulfides, sulfur or sulfites.

9 Claims, No Drawings

METHOD FOR PRODUCING THIOCTIC ACID

The invention relates to a method for producing thioctic acids of the general formula III in the form of the racemate and of the R- and S-enantiomers and mixtures thereof in high yield and purity.

When the term thioctic acid is used below, it is always to be understood as meaning both the racemic mixture (R,S-thioctic acid) and the pure enantiomeric compounds (R- and S-thioctic acid) and mixtures having any desired contents of enantiomers.

Thioctic acid is pharmacologically active and has antiphlogistic, antinociceptive and cytoprotective properties (EP 0427247).

An important medical indication of racemic thioctic acid is high-dose long-term therapy of diabetic polyneuropathy.

Thioctic acid may also become important in fighting diseases caused by HIV-1 and HTLV III B viruses (A. Baur, et al., Klin. Wochenschr. 1991, 69, 722; J. P. Merin et al., FEBS Lett. 1996, 394, 9).

The R-enantiomer of thioctic acid is a natural substance which occurs in low concentrations in virtually all animal and plant cells. R-Thioctic acid is essential as a coenzyme in the oxidative decarboxylation of α-ketocarboxylic acids (e.g. pyruvic acid).

Among the pure optical isomers of thioctic acid, the R-enantiomer has predominantly antiphlogistic activity and the S-enantiomer predominantly antinociceptive activity (EP 0427247). Different pharmacokinetic properties of the two enantiomers are also found (e.g. R. Hermann et al., Eur. J. Pharmaceut. Sci. 1995, 4, 1967). Both the synthesis of the racemate and that of the pure enantiomers are therefore of considerable importance.

A known principle for producing thioctic acids of the general formula III consists in the reaction of 6,8-disubstituted octanoic acids or their alkali metal salts and esters of the general formula I, in which X, Y, R and R' have the meaning stated below and X and Y may be identical or different, with a sulfurization reagent which is prepared from equimolar amounts of sodium sulfide and sulfur and, owing to its stoichiometric composition, is frequently referred to as sodium disulfide ($Na_2S_2$), or in the joint action of sodium sulfide ($Na_2S$) and sulfur on the compounds of the general formula I (D. S. Acker and W. J. Wayne, J. Am. Chem. Soc. 1957, 17, 6483; A. V. Rama Rao et al., Synth. Commun. 1987, 17, 1339; M. H. Brookes et al., J. Chem. Soc. Perkin Trans. I 1988, 9; P. C. B. Page et al., J. Chem. Soc. Perkin Trans I 1990, 1615; A. S. Gopalan et al., J. Chem. Soc. Perkin Trans. I 1990, 1897; J. S. Yadav et al., J. Carbohydrate Chem., 1990, 9, 307; DE 19533881; G. Bringmann et al., Z. Naturforsch. 54b, 655 (1999)).

The compounds of the general formula I can be used both as the racemate and in the form of the R- and S-enantiomers or mixtures thereof.

The relevant procedure is one in which the compounds of the general formula I are added to a solution of the sulfurization reagent in a solvent, such as ethanol or DMF. In the case of the acids of the general formula I, R=H, sodium sulfide and sulfur are added together to the alkali metal salt of the acid.

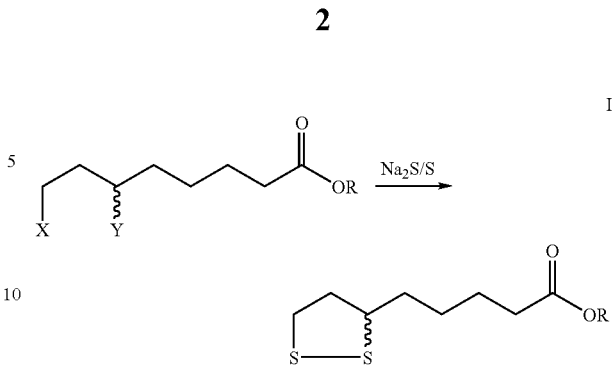

X, Y=Cl, Br, $OSO_2R'$ II R=$C_{1-4}$-alkyl
R'=$C_{1-4}$-alkyl, aryl III R=H
R=H, K, Na, $C_{1-4}$-alkyl The esters II initially obtained in the case of R=$C_{1-4}$-alkyl are then hydrolyzed by adding alkali in a homogeneous medium to give the thioctic acid III. Long reaction times are required both in the introduction of sulfur to give II and in the hydrolysis to give III (e.g. A. V. Rama Rao et al., Synth. Commun. 1987, 17, 1339: 24 h).

The thioctic acids III obtained under the stated conditions are, however, contaminated to an extent of several percent by the compounds IV and V, which may be present in the form of the racemates or as R- or S-enantiomers.

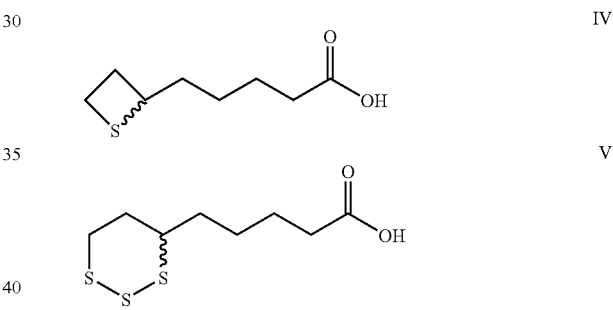

Since the compounds IV and V differ structurally from thioctic acid only in the number of sulfur atoms, the differences in the physicochemical properties, such as, for example, volatility and solubility, which are required for economic separation and purification operations, such as distillation and recrystallization, are only small. The subsequent separation of the byproducts IV and V formed during the reaction is extremely complicated and therefore not possible in an economical manner. Detection is possible only by special analytical methods, such as, for example, HPLC. The fact that the compounds IV and V were also formed in the methods known to date is not surprising since it is generally known that a mixture of sulfides ($Na_2S_x$) of different chain length x forms in the reaction of sodium sulfide ($Na_2S$) with sulfur. As a result of this, the reaction of 6,8-disubstituted octanoic acids and their alkali metal salts and esters with sodium sulfide/sulfur (molar ratio 1:1), not only is the thioctic acid expected on the basis of the stoichiometry formed (x=2, incorporation of an $S_2$ unit), but, by incorporation of "$S_1$" (when x=1), 5-(2-thiacyclobutylvaleric acid IV and, by incorporation of "$S_3$" (when x=3), 5-(1,2,3)trithian-4-ylpentanoic acid V, in addition to higher aliphatic and cyclic polysulfides, are formed.

The quality problems associated with the one-stage direct introduction of sulfur into 6,8-disubstituted octanoic acids and their alkali metal salts and esters of the general formula I were therefore frequently circumvented by first reducing the crude thioctic acid by means of NaBH$_4$ to 6,8-dimercaptooctanoic acid, which had to be oxidized in a further stage to thioctic acid (e.g. DE 1953381).

As a result, however, only a decrease in the concentration of the compound V degradable by reduction to 6,8-dimercaptooctanoic acid is achieved, but not the removal of IV.

Even more complicated is the introduction of sulfur via the reaction of the 6,8-disubstituted octanoic acids and their esters with thiourea to give the salts of 6,8-bis(amidiniumthio)octanoic acid, the cleavage thereof to give 6,8-dimercaptooctanoic acid and oxidation to give thioctic acid (3-stage method, e.g. F. Balkenhohl and J. Paust, Z. Naturforsch. 54b, 649 (1999); DE 19601787).

In summary, it may be stated that the procedure described is poor and an economical method for producing pure thioctic acid of the general formula III does not exist. The provision of pure thioctic acid is, however, particularly important also because of the abovementioned high-dose long-term therapy.

It is therefore an object of the invention to provide an economical production process for the compound III in high purity and yield.

This object is achieved if first a sulfide of the general formula VI

　　　　　　　　　　　　　　　　　　　　VI in which M is an alkali metal ion or an ammonium ion, is metered into a mixture consisting of suspended sulfur and the solution of a racemic, (R)- or (S)-6,8-disubstituted octanoic acid, the corresponding alkali metal salts and alkyl esters of the general formula I, and then a sulfite of the general formula VII

　　　　　　　　　　　　　　　　　　　　VII in which M' is an alkali metal ion, an ammonium ion or half an alkaline earth metal ion, is allowed to act. It is also possible to use mixtures of the compounds of the general formula I. The sulfide VI may be metered in in solid form or in aqueous or aqueous alcoholic solution. The aqueous alcoholic solution may be a mixture of water and a lower alcohol having 1 to 3 C atoms. The sulfite VII may be added as a solid salt or in aqueous solution.

In the case of the esters of the general formula I, R=C$_{1-4}$-alkyl, it is also possible to add the sulfite of the general formula VII in the beginning or during the alkaline hydrolysis of II to III. Furthermore, the sulfite of the general formula VII can also be added in each case in portions after the addition of the sulfide of the general formula VI and at the beginning or during the alkaline hydrolysis of II to III.

Suitable inert, water-miscible solvents for the compounds of the general formula I are both polar, protic solvents, such as lower alcohols having 1 to 3 C atoms, and dipolar aprotic solvents, such as, for example, dimethylformamide, N-methylpyrrolidone or acetone, and nonpolar solvents, such as, for example, toluene or n-heptane. The stated solvents may also be used as mixtures.

It is also possible to use mixtures of water both with the pure solvents and with the solvent mixtures. The molar ratio I:VI:sulfur:VII is 1:1:1:0.5 to 1:1.5:2 3, preferably 1:1.1: 1.5:1 to 1:1.1 1.5:2

The introduction of sulfur can be carried out at temperatures of 0 to 100° C., preferably in the range from 5 to 90° C.

In special cases, such as, for example, with the use of the (S)- and (R)-8-chloro-6-sulfonyloxyoctanoic acids, the corresponding alkali metal salts and alkyl esters of the general formula I (X=Cl, Br, Y=OSO$_2$R'), it is necessary, in order to avoid racemizations, to vary the reaction temperature in steps by carrying out the sulfide addition at 30–50° C., preferably 30–45° C., and only thereafter increasing the reaction temperature. The alkaline hydrolysis of II to III is effected under mild conditions in the two-phase system cyclohexane or methyl tert-butyl ether/dilute alkali solution at temperatures of 30 to 90° C., usually with reaction times <5 h.

The reaction times both in the introduction of sulfur to give II and in the hydrolysis to give III are substantially shortened compared with the prior art. Depending on the octanoic acid derivative I used, the thioctic acids III are obtained in yields of up to more than 80% in very pure form without the compounds IV and V.

In a particular embodiment of the invention, it is also possible, in a procedure otherwise according to the invention, to dispense with the addition of the sulfite of the general formula VII during the reaction of I to give II or to give III and initially to isolate the crude products particularly highly contaminated with the compound V.

The pure products can be obtained by action of sulfites of the general formula VII, optionally in the presence of inert solvents, such as cyclohexane or methyl tert-butyl ether, on the crude products dissolved in dilute alkali solutions. Below, the invention is explained in more detail with reference to examples, but without restricting it.

EXAMPLE 1

A solution of 4.0 g (0.1 mol) of sodium hydroxide in 10 ml of water is added to 100 ml of ethanol (96%), and 21.3 g (0.1 mol) of rac. 6,8-dichlorooctanoic acid (D. S. Acker and W. J. Wayne, J. Amer. Chem. Soc. 1957, 79, 6483) and 4.8 g (0.15 mol) of sulfur are added in succession with stirring. The mixture is gently refluxed (internal temperature 70–80° C.). A solution of 13.8 g (0.11 mol) of sodium sulfide hydrate (content: 62% of Na$_2$S), dissolved in a mixture of 70 ml of water and 40 ml of ethanol (96%), is added dropwise with stirring in the course of about 2 h with gentle refluxing.

A solution of 18.9 g (0.15 mol) of sodium sulfite in 75 ml of water is then allowed to run in, and stirring is continued for 1 h at an internal temperature of about 80° C. Cooling to about 50° C. is effected and 600 ml of water and 250. ml of a 4:1 cyclohexane/ethyl acetate mixture are added. At 35–40° C., acidification is effected with 10% strength hydrochloric acid with stirring (pH 1). The phases are separated, extraction is effected with twice 100 ml of 4:1 cyclohexane/ethyl acetate at 35–40° C. and the combined organic phases are evaporated down in vacuo under mild conditions (bath temperature up to 40° C.). Cooling is effected to 0 to 5° C. with stirring (beginning of crystallization) and then for 2 to 3 h at –5 to –10° C. After washing with cold cyclohexane and drying (30° C.), 17.7 to 18.4 g (86–89% of theory) of pure R,S-thioctic acid are obtained. M.p. 61° C. (from 4:1 cyclohexane/ethyl acetate)

EXAMPLE 2

24.1 g (0.1 mol) of ethyl 6,8-dichlorooctanoate and then 4.8 g (0.15 mol) of sulfur are added with stirring to a mixture of 50 ml of ethanol and 50 ml of n-propanol. After heating to an internal temperature of 82 to 84° C. (reflux), a solution of 13.8 g (0.11 mol) of sodium sulfide hydrate (content: 62% of Na$_2$S) in 80 ml of water and 40 ml of ethanol is added dropwise with thorough stirring in the course of 2 to 2.5 h.

A solution of 18.9 g (0.15 mol) of sodium sulfite in 75 ml of water is then added rapidly and heating is continued for a further 1 h with gentle refluxing. Cooling is effected to about 50° C., 200 ml of cyclohexane and 300 ml of water are added, the pH is adjusted to about 1 with 10% strength hydrochloric acid at an internal temperature of 30 to 35° C. with stirring, and stirring is continued for about 15 min. The phases are separated, the cyclohexane phase is added to a solution of 8 g (0.2 mol) of sodium hydroxide in 600 ml of water and the two-phase system is stirred thoroughly for about 4 h at an internal temperature of about 70° C. (gentle refluxing).

Cooling is effected to about 50° C., the phases are separated, 500 ml of cyclohexane/ethyl acetate (95:5) are added to the aqueous phase and acidification is effected with about 10% strength hydrochloric acid at an internal temperature of 35 to 40° C. with stirring (pH 1 to 2). After the phase separation, extraction is effected with a further 200 ml of cyclohexane/ethyl acetate (95:5).

The combined organic phases are stirred with 1 g of Diacel 300 BL (filtration aid) for about 10 min at about 30° C. and, after filtration in vacuo at a bath temperature of not more than 40° C., the solution is evaporated down to about 200 ml. Crystallization is allowed to take place with stirring at −5 to −10° C. for 4 to 6 h. After washing with cold cyclohexane and drying at 30° C., 14.6 to 15.7 g (71 to 76% of theory) of pure R,S-thioctic acid are obtained.

M.p. 61° C. (from cyclohexane/ethyl acetate)

EXAMPLE 3

4.8 g (0.15 mol) of sulfur are added with stirring to a solution of 22.7 g (0.1 mol) of methyl (S)-6,8-dichlorooctanoate (DE 19533881) in a mixture of 50 ml of ethanol and 50 ml of n-propanol.

Heating is effected to an internal temperature of 82 to 84° C. (reflux) and a solution of 13.8 g (0.11 mol) of sodium sulfide hydrate (content: 62% of Na$_2$S in 80 ml of water and 40 ml of ethanol is added dropwise with thorough stirring in the course of about 2 h.

Thereafter, a solution of 18.9 g (0.15 mol) of sodium sulfite in 75 ml of water is added rapidly, stirring is continued for a further 1 h with gentle refluxing, cooling is effected to 40–50° C., 200 ml of methyl tert-butyl ether (MTBE) and 300 ml of water are added, acidification is effected with 10% strength hydrochloric acid at an internal temperature of 30–35° C. (pH 1–2) and stirring is continued for 15 min. The phases are separated, the MTBE phase is added to a solution of 8 g (0.2 mol) of caustic soda in 600 ml of water and the two-phase system is stirred thoroughly for 2–3 h at an internal temperature of about 55° C. (reflux). Cooling is effected to 40–50° C., the phases are separated and 300 ml of cyclohexane are added to the aqueous phase.

At 35–40° C., acidification is effected with 10% strength hydrochloric acid with stirring (pH 1–2). The phases are separated, extraction is effected with 300 ml of cyclohexane at 35–40° C., the combined cyclohexane phases are stirred for 10 min with 1 g of Diacel 300 BL (filtration aid) at 35 to 40° C., filtration is effected and the solution is evaporated down in vacuo at not more than 35° C. to about 30% of the original volume. Stirring is effected for 2 to 3 h at 6–10° C., and the crystals are washed with cold cyclohexane (2×5 ml) and dried at room temperature.

Yield: 15.2 to 16.3 g (74–79% of theory) of pure R-thioctic acid. M.p. 49–50° C. (from cyclohexane)

EXAMPLE 4

A solution of 28.7 g (0.1 mol) of methyl (S)-8-chloro-6-mesyloxyoctanoate (DE 19533881) in toluene (66% strength solution, 43.5 g) is added to 50 ml of ethanol and 50 ml of n-propanol, and 4.8 g (0.15 mol) of sulfur are added with stirring, heating is effected to an internal temperature of 40–42° C. and a solution of 13.8 g (0.11 mol) of sodium sulfide hydrate (content: 62% of Na$_2$S) in 80 ml of water and 40 ml of ethanol is added dropwise with thorough stirring in the course of 1 h. Refluxing (80 to 84° C.) is effected, a solution of 18.9 g (0.15 mol) of sodium sulfite in 75 ml of water is added dropwise in the course of 1 h and stirring is continued for 1 h under reflux. Thereafter, cooling is effected to 40–50° C., 200 ml of cyclohexane and 300 ml of water are added, acidification is effected with 10% strength hydrochloric acid at an internal temperature of 30–35° C. (pH 1–2) and stirring is continued for 15 min. The phases are separated, the cyclohexane phase is added to a solution of 8 g (0.2 mol) of caustic soda in 600 ml of water and the two-phase system is stirred thoroughly for 2–3 h at an internal temperature of about 60° C. Cooling to 40–50° C. is effected, the phases are separated and 300 ml of cyclohexane are added to the aqueous phase.

At 35–40° C., acidification is effected with 10% strength hydrochloric acid with stirring (pH 1–2). The phases are separated, extraction is effected with 300 ml of cyclohexane at 35–40° C., the combined cyclohexane phases are stirred for 10 min with 1 g of Diacel 300 BL (filtration aid), filtration is effected and the solution is evaporated down in vacuo up to a bath temperature of 40° C. to about 30% of the original volume. Stirring is effected for 2 to 3 h at 5–10° C., and the crystals are washed with cold cyclohexane (2×5 ml) and dried at room temperature.

Yield: 15.2 to 16.3 g (−74 to 79% of theory) of pure R-thioctic acid. M.p. 49–50° C. (from cyclohexane)

EXAMPLE 5

4.8 g (0.15 mol) of sulfur are added with stirring to a solution of 22.7 g (0.1 mol) of methyl (S)-6,8-dichlorooctanoate (DE 19533881) in a mixture of 50 ml of ethanol and 50 ml of n-propanol.

Heating is effected to an internal temperature of 82 to 84° C. (reflux) and a solution of 13.8 g (0.11 mol) of sodium sulfide hydrate (content: 62% of Na$_2$S) in 80 ml of water and 40 ml of ethanol is added dropwise with thorough stirring in the course of about 2 h.

Thereafter, stirring is effected for a further 1 h with gentle refluxing, cooling is effected to 40 to 50° C., 200 ml of cyclohexane and 300 ml of water are added, acidification is effected with 10% strength hydrochloric acid at an internal temperature of 30 to 35° C. (pH 1–2) and stirring is continued for 15 min. The phases are separated, the cyclohexane phase is added to a solution of 8 g (0.2 mol) of sodium hydroxide and 18.9 g (0.15 mol) of sodium sulfite in 600 ml of water, and the two-phase system is stirred thoroughly for 2 h at an internal temperature of about 60° C. Cooling is effected to 40–50° C., the phases are separated and 300 ml of cyclohexane are added to the aqueous phase. At 35–40° C., acidification is effected with 10% strength hydrochloric acid with stirring (pH 1–2). The phases are separated, extraction is effected with 300 ml of cyclohexane at 35–40° C., the combined cyclohexane phases are stirred for 10 min with 1 g of Diacel 300 BL (filtration aid) at 35 to 40° C., filtration is effected and the solution is evaporated down in vacuo at a bath temperature of not more than 40° C.

to about 30% of the original volume. Stirring is effected for 2–3 h at 5–10° C., and the crystals are washed with cold cyclohexane (2×5 ml) and dried at room temperature.

Yield: 14.4 to 15.2 g (70–74% of theory) of pure R-thioctic acid. M.p. 49–50° C. (from cyclohexane)

EXAMPLE 6

4.8 g (0.15 mol) of sulfur are added with stirring to a solution of 22.7 g (0.1 mol) of methyl (S)-6,8-dichlorooctanoate (DE 19533881) in a mixture of 50 ml of ethanol and 50 ml of n-propanol. Heating to an internal temperature of 82 to 84° C. is effected (reflux), a solution of 13.8 g (0.11 mol) of sodium sulfide hydrate (content: 62% of $Na_2S$) in 80 ml of water and 40 ml of ethanol is added dropwise with thorough stirring in the course of about 2 h, and a solution of 9.5 g (0.075 mol) of sodium sulfite in 40 ml of water is added. Thereafter, stirring is effected for a further 1 h with gentle refluxing, cooling is effected to 40 to 50° C., 200 ml of cyclohexane and 300 ml of water are added and acidification is effected with 10% strength hydrochloric acid at an internal temperature of 30 to 35° C. (pH 1–2). The phases are separated, the cyclohexane phase is added to a solution of 8 g (0.2 mol) of sodium hydroxide and 9.5 g (0.075) of sodium sulfite in 600 ml of water and the two-phase system is stirred thoroughly for 2 h at an internal temperature of 68–70° C. (reflux). Cooling is effected to 40–50° C., the phases are separated and 300 ml of cyclohexane are added to the aqueous phase. At 35–40° C., acidification is effected with 10% strength hydrochloric acid with stirring (pH 1–2). The phases are separated, extraction is effected with 300 ml of cyclohexane at 35–40° C., the combined cyclohexane phases are stirred for 10 min with 1 g of Diacel 300 BL (filtration aid) at 35 to 40° C., filtration is effected and the solution is evaporated down in vacuo at a bath temperature of not more than 40° C. to about 30% of the original volume. Stirring is effected for 2–3 h at 6–10° C., and the crystals are washed with cold cyclohexane (2×5 ml) and dried at room temperature.

Yield: 15.0 to 16.1 g (73–78% of theory) of pure R-thioctic acid

EXAMPLE 7

Purification of Crude Thioctic Acid 5.1 g of crude R-thioctic acid. (content of V: 14%) and 4 g of sodium sulfite were introduced into dilute sodium hydroxide solution (1 g of NaOH dissolved in 150 ml of water). The solution was stirred for 3 h at an internal temperature of 60–62° C. After cooling, 75 ml of cyclohexane were added and acidification with dilute hydrochloric acid was effected at 35–40° C. with stirring (pH 1–2). After the phase separation, extraction was effected with 75 ml of cyclohexane at 35 to 40° C. The combined extracts were evaporated down in vacuo at a maximum bath temperature of 40° C. to about ¼ of the volume. The solution was stirred for 2–3 h at 5–10° C., and the crystals were washed with cold cyclohexane and dried at room temperature.

Yield: 4.1 g of pure R-thioctic acid M.p. 50 to 51° C.

The invention claimed is:

1. A method for producing racemic, R- or S-thioctic acid or mixtures thereof of the general formula III, characterized in that the solution of a sulfide of the general formula VI is metered into a mixture consisting of suspended sulfur and a solution of a racemic, (R)- or (S)-6,8-disubstituted octanoic acid, the corresponding alkali metal salts, alkyl esters and mixtures of the general formula I, in which X, Y, R and R' have the meanings stated below, and then, optionally during or after the hydrolysis of an ester II formed as an intermediate, a sulfite of the general formula VII is allowed to act.

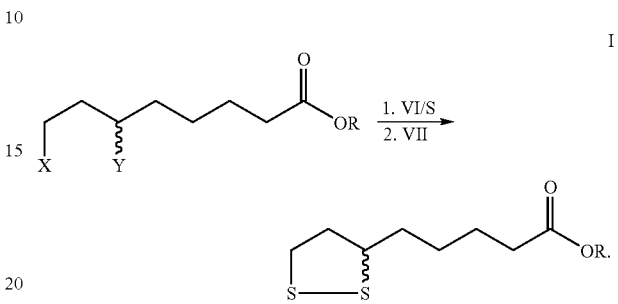

X, Y=Cl, Br, $OSO_2R'$ II $R=C_{1-4}$-alkyl
$R'=C_{1-4}$-alkyl, aryl III R=H
R=H, K, Na, $C_{1-4}$-alkyl
$M_2S$ $M'_2SO_3$
VI VII
$M=K, Na, NH_4$ $M'=K, Na, NH_4, Mg/2, Ca/2, Ba/2$ 2. The method as claimed in claim 1, characterized in that the molar ratio I:VI:sulfur:VII is 1:1:1:0.5 to 1:1.5:2:3.

3. The method as claimed in claim 1, characterized in that, with the use of the racemic, (R)- or (S)-6,8-disubstituted octanoic esters or mixtures thereof of the general formula I ($R=C_{1-4}$-alkyl), the initially formed racemic, R- or S-thioctic ester of the general formula II is hydrolyzed to give racemic, R- or S-thioctic acid or mixtures thereof of the general formula III.

4. The method as claimed in claim 1, characterized in that the sulfide of the general formula VI is metered in in the form of an aqueous or aqueous alcoholic solution.

5. The method as claimed in claim 1, characterized in that polar protic solvents, dipolar aprotic solvents, nonpolar solvents, mixtures of said solvents and mixtures with water are used as solvents for the compounds of the general formula I.

6. The method as claimed in claim 1, characterized in that the sulfite of the general formula VII is added as a solid salt or in the form of an aqueous solution.

7. A method for hydrolyzing crude racemic, R- or S-thioctic esters of the general formula II in the two-phase system to give pure racemic R- or S-thioctic acid or mixtures thereof in the presence of sulfites of the general formula VI.

8. A method for purifying racemic, R- or S-thioctic acid or mixtures thereof by the action of sulfites of the general formula VI, optionally in the presence of inert solvents, on the crude products dissolved in dilute alkali solutions.

9. The method of claim 2, characterized in that the molar ratio I:VI:sulfur:VII is 1:1.1:1.5:1 to 1:1.1:1.5:2.

* * * * *